Figure 1:
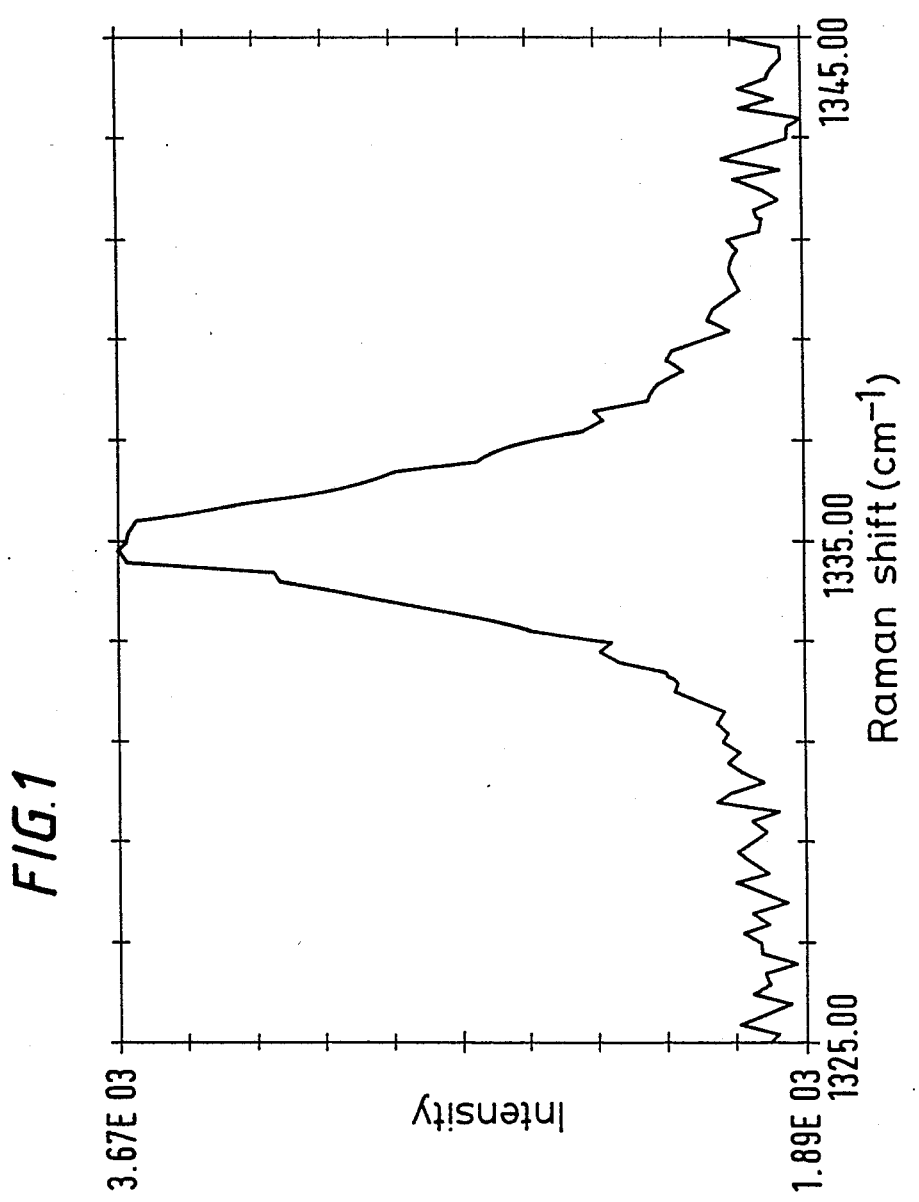

United States Patent [19]

Bowley et al.

[11] Patent Number: 4,900,147

[45] Date of Patent: Feb. 13, 1990

[54] DIAMOND MAPPING

[75] Inventors: Heather J. Bowley, Middlesex; Donald L. Gerrard, Surrey, both of England

[73] Assignee: The British Petroleum Company, p.l.c., England

[21] Appl. No.: 275,145

[22] PCT Filed: Mar. 10, 1988

[86] PCT No.: PCT/GB88/00188

§ 371 Date: Nov. 15, 1988

§ 102(e) Date: Nov. 15, 1988

[87] PCT Pub. No.: WO88/07189

PCT Pub. Date: Sep. 22, 1988

[30] Foreign Application Priority Data

Mar. 18, 1987 [GB] United Kingdom ............... 8706422

[51] Int. Cl.$^4$ .................. G01J 3/44; G01N 21/65; G01N 21/87
[52] U.S. Cl. ........................................ 356/30; 356/301
[58] Field of Search ................................ 356/30, 301

[56] References Cited

U.S. PATENT DOCUMENTS 3,947,120 3/1976 Bar-Issac et al. ................. 356/30
4,030,827 6/1977 Delhaye et al. .................. 356/301
4,397,556 8/1983 Müller ............................ 356/301

FOREIGN PATENT DOCUMENTS 2496888 6/1982 France .
2571144 4/1986 France .
86/07457 12/1986 PCT Int'l Appl. .
87/03963 7/1987 PCT Int'l Appl. .
1547371 6/1979 United Kingdom .
2191282 12/1987 United Kingdom .

OTHER PUBLICATIONS

Field, J. E., *The Properties of Diamond*, "Colour Centres and Optical Properties" (Academic Press, 1979) pp. 23–77.

"Image Visualization", *Physical Encyclopaedical Dictionary, Moscow Soviet Encyclopaedia* (1983), p. 76. (with translation).

"Optical Radiation Receivers", *Physical Encyclopaedical Dictionary, Moscow Soviet Encyclopaedia* (1983), pp. 585, 586 (with translation).

Long, D. A., "The Renaissance of Raman Spectroscopy", *Chemistry in Britian* (Jun. 1989), pp. 589–590.

Long, D. A., "Linear and Nonlinear Raman Effects: The Principles", *Chemistry in Britain* (Jun. 1989), pp. 592–596.

Corset, J. et al., "Raman Microscopy", *Chemistry in Britain*, (Jun. 1989), pp. 612–616.

S. A. Solin and A. K. Ramdas, Physical Review B., vol. 1, No. 4, Feb. 15, 1970, pp. 1687–1698, "Raman Spectrum of Diamond".

*Primary Examiner*—F. L. Evans
*Attorney, Agent, or Firm*—Joseph G. Curatolo; George W. Moxon, II; Larry W. Evans

[57] ABSTRACT

A method for mapping the crystal structure of a diamond comprises placing the diamond in a beam of monochromatic laser radiation, filtering the resultant scattered Raman radiation, and measuring the intensity of the filtered radiation at one or more different orientations of the diamond which may be compared with records of known diamonds to identify the diamond.

17 Claims, 5 Drawing Sheets

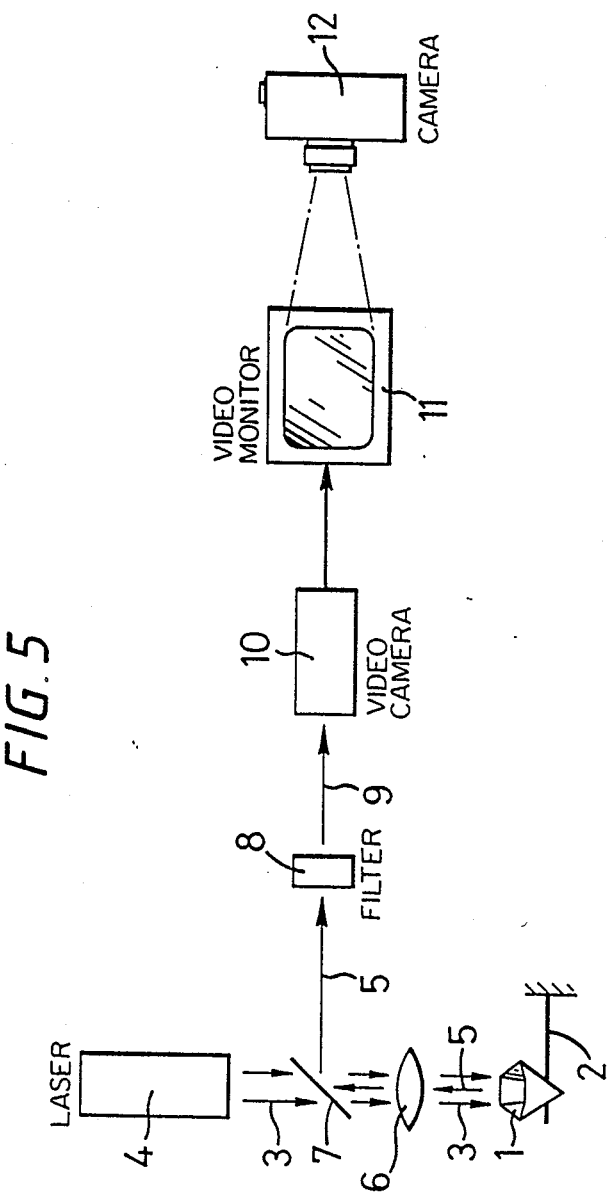

DIAMOND MAPPING

The present invention relates to diamond mapping and in particular to a method for mapping the crystal structure of a diamond.

Diamonds have long been recognised as being of great value not only for decorative and industrial purposes but also as an investment. Their increasing value has presented problems of security for owners, insurance companies and police authorities. Identification of a recovered diamond which has been lost or stolen is made difficult because the superficial appearance of the diamond may have been changed by cutting, repolishing and the like. Conventionally, the recognition of diamond has been achieved on the basis of a record of characteristics comprising carat weight, cut, colour type, clarity etc.

More recently, X-ray topography has been used for identifying diamonds, as is disclosed in UK Patent No. 1,547,371. In this technique a set of records is produced by X-ray topography to provide an overall point-by-point three-dimensional representation of the diamond. The set of records of a recovered diamond that has been lost or stolen may be compared with the sets of records of known diamonds as a means of identifying the recovered diamond. However, this technique may be slow and requires interpretation of the diffraction patterns to produce the sets of records of defects.

The Raman signal of diamond is much stronger than that of other materials because diamond only contains carbon to carbon bonding and its Raman signal occurs at a position well separated from those of other minerals. Also, as diamond only contains one type of carbon to carbon bond, there is only a single Raman signal which can be readily distinguished from associated broad band fluorescence. Thus the Raman signal is highly specific for diamond. The intensity of the Raman signal is affected by the crystal structure of the diamond and hence by the presence or otherwise of imperfections or inclusions in the diamond. For example, it has been found that imperfections cause a broadening of the diamond Raman signal and inclusions do not give a diamond Raman signal.

Thus according to the present invention there is provided a method for mapping the crystal structure of a diamond, the method comprising the steps of (a) placing the diamond in a beam of monochromatic laser radiation capable of causing Raman radiation to be scattered from the diamond, (b) passing the scattered Raman radiation from the diamond through a filter adapted to pass only scattered Raman radiation characteristic of diamond, and (c) measuring the intensity of the filtered Raman radiation at one or more different orientations of the diamond.

Also, according to the present invention there is provided a method for producing a record of a diamond, the method comprising the steps of (a) placing the diamond in a beam of monochromatic laser radiation capable of causing Raman radiation to be scattered from the diamond, (b) passing the scattered Raman radiation from the diamond through a filter adapted to pass only scattered Raman radiation characteristic of diamond, (c) measuring the intensity of the filtered Raman radiation, and (d) recording the intensity of the filtered Raman radiation at one or more different orientations of the diamond.

The invention also includes records whenever produced by the method as hereinbefore described.

According to the present invention there is also provided an apparatus for producing a record of a diamond, the apparatus comprising in combination (a) means for holding the diamond in a beam of monochromatic laser radiation capable of causing Raman radiation to be scattered from the diamond, (b) means for filtering the resultant scattered Raman radiation, said filter being adapted to pass only scattered Raman radiation characteristic of diamond, (c) means for measuring the intensity of the filtered Raman radiation, and (d) means for recording the intensity of the filtered Raman radiation at one or more different orientations of the diamond to produce a record of the diamond.

Preferably, the Raman intensities are recorded at three mutually perpendicular orientations of the diamond.

The record of the diamond may be used for identification purposes. Thus the record of a recovered diamond that has been lost or stolen may be compared with records of known diamonds so that it may be identified. Thus, also, according to the present invention there is provided a method for identifying a diamond, the method comprising the steps of (a) placing the diamond to be identified in a beam of monochromatic laser radiation capable of causing Raman radiation to be scattered from the diamond, (b) passing the scattered Raman radiation from the diamond through a filter adapted to pass only scattered Raman radiation characteristic of diamond, (c) measuring the intensity of the filtered Raman radiation, (d) recording the intensity of the filtered Raman radiation at one or more different orientations of the diamond, and (e) comparing the recorded intensities with records of known diamonds whereby the diamond may be identified.

Preferably the monochromatic laser radiation has a wavelength in the range 450 to 650 nanometers. The filtering means may be a suitable optical arrangement such as a collection optic and monochromator. Preferably, the scattered Raman radiation is focused by a suitable lens arrangement with a long depth of focus so that the scattered Raman radiation from throughout the diamond is in focus at the detector.

The record may be a point-by-point record of the Raman intensities or may be a record of the Raman intensities from the whole of the diamond simultaneously. Thus in the former case the record may be in the form of values stored on magnetic tape or in a computer etc. and in the latter case the record may be in the form of a photograph.

In one embodiment of the present invention a video or television camera may be adapted to display the scattered Raman intensities on a monitor or television screen. It is envisaged that in this embodiment the invention may enable the crystal structure of a diamond to be mapped for a large number of orientations of the diamond without the delay imposed by photographic developing or interpretation of diffraction patterns etc. A record may be made in the form of images stored by conventional means e.g. video tape, for different orientations of the diamond, and may be used for future identification purposes.

In another embodiment of the present invention, a photomultiplier or multichannel detector (e.g. diode array detector) may be adapted to scan the scattered Raman radiation. It is also envisaged that the means for holding the diamond in the laser radiation may be adapted so that the orientation of the diamond may be changed under automatic, microprocessor or computer control. A record of the diamond may be made in the form of stored Raman intensities which may be stored by conventional means, for example in a computer or on magnetic tape etc. In this embodiment it may be possible for a computer to control the orientation of the diamond and the production of the record so that a three-dimensional record of the diamond may be produced. This may be stored by conventional means such as in a computer or on magnetic tape or as a hologram, produced under the control of a computer.

In another embodiment of the present invention the filtered Raman radiation may be measured and recorded by a camera with a photographic plate or film sensitive to the filtered Raman radiation. The plate or film is suitably processed to produce a two-dimensional image of the scattered Raman intensity of the diamond in the selected orientation. The record of the diamond may take the form of several such photographic images at different orientations of the diamond and may be used for future identification purposes.

The invention will now be described by way of example only, and with reference to the accompanying drawings. FIGS. 1 to 4 show graphically, the Raman intensities from various parts of a diamond with an imperfection. FIG. 5 shows, in schematic form, an apparatus which may be used to map the crystal structure of a diamond and to produce a record of the diamond which may be used for future identification purposes.

Figure 2:
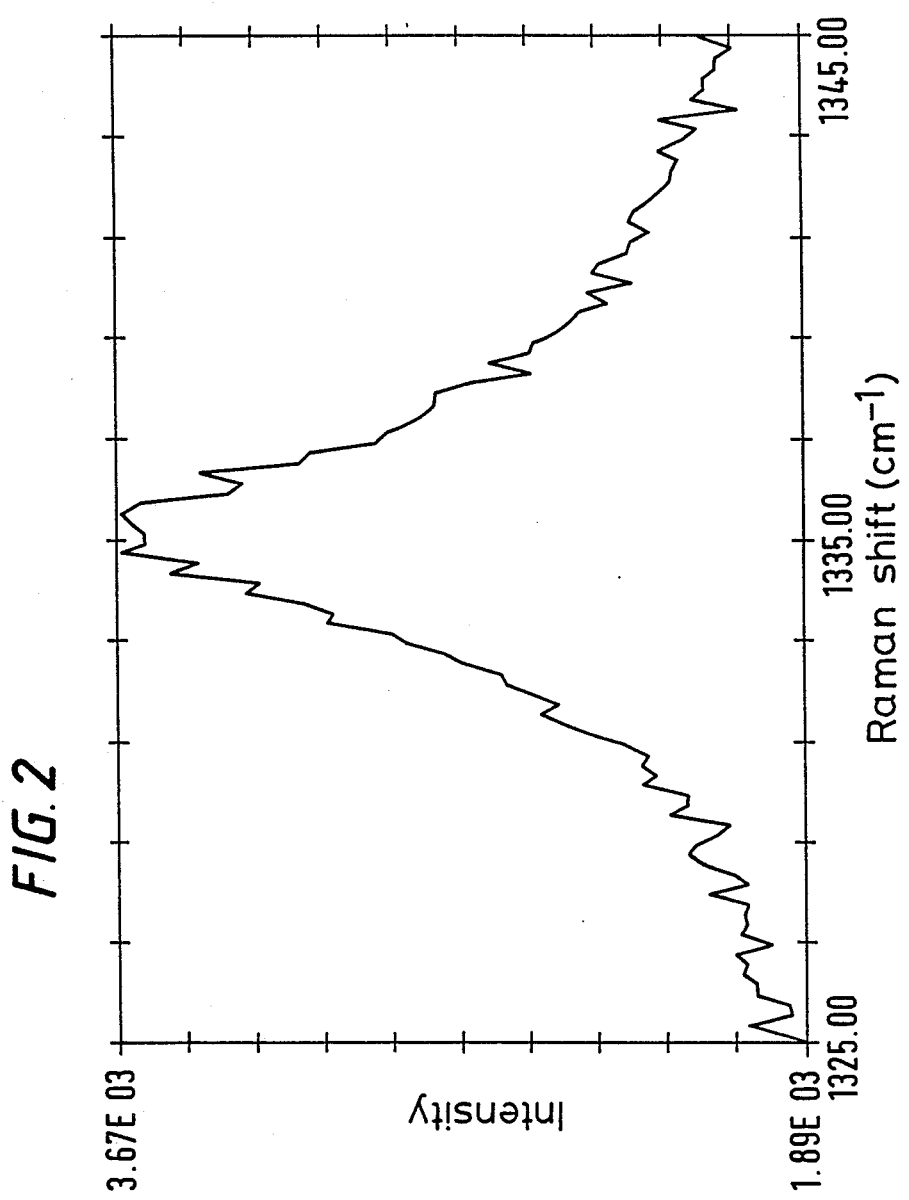
Figure 3:
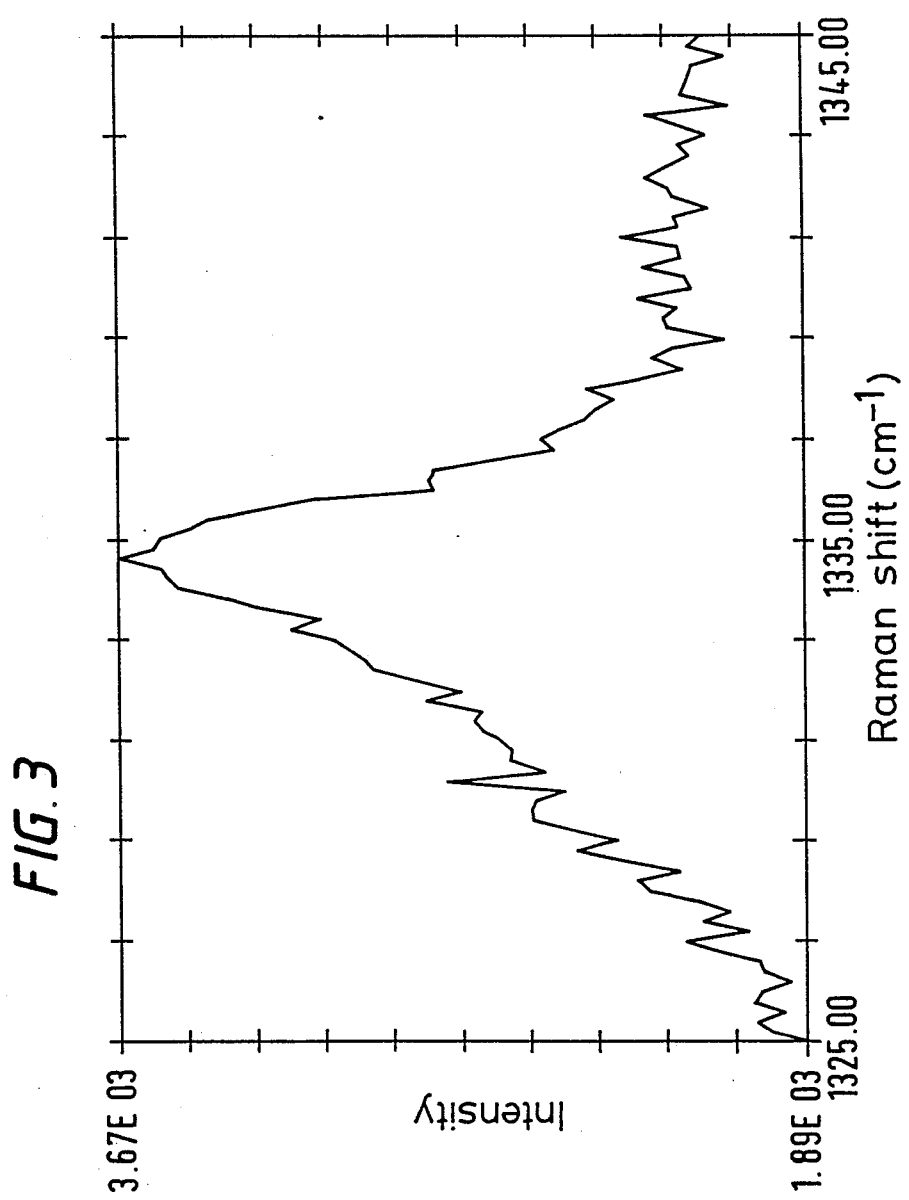
Figure 4:
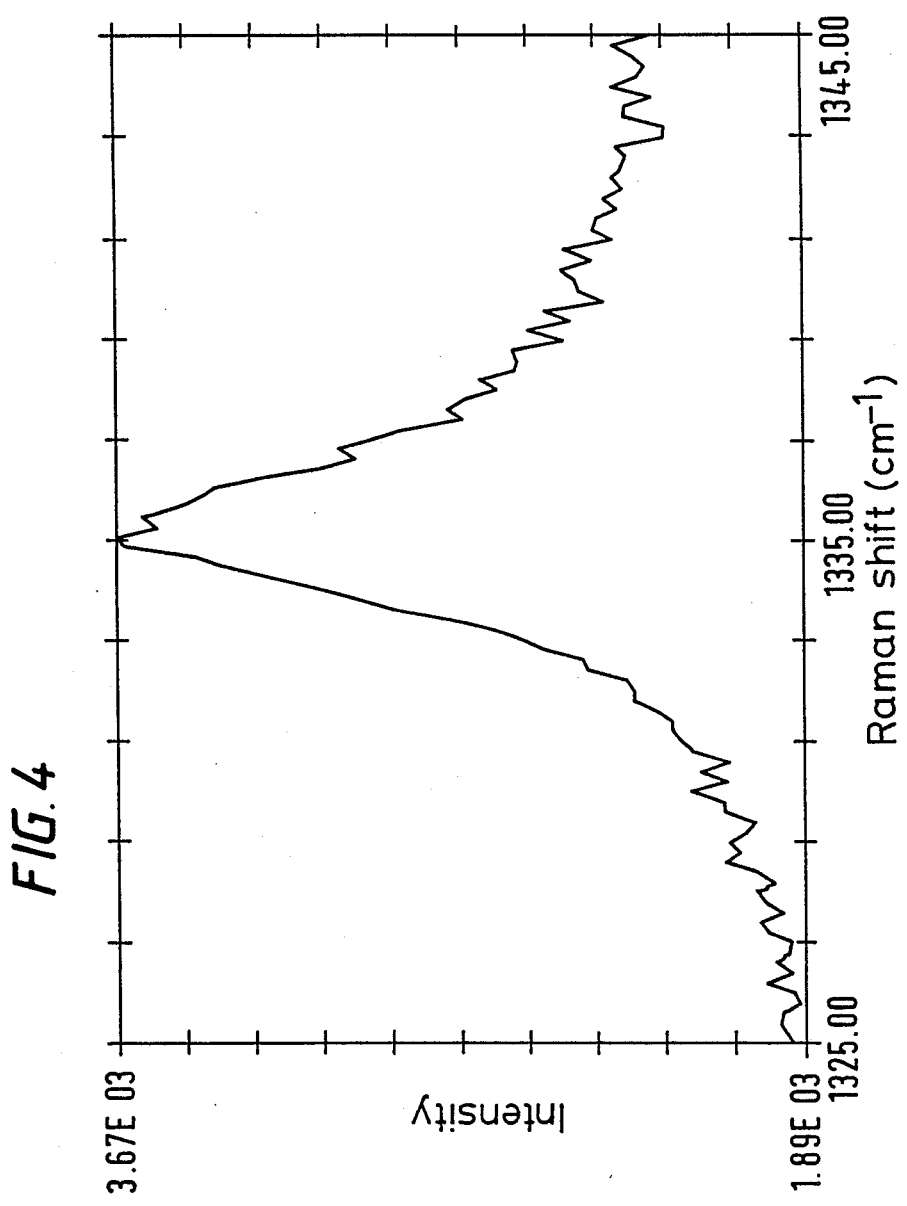

To show that Raman spectroscopy may be used to map the crystal structure of a diamond to show an imperfection, a series of Raman spectrograms were recorded in the region of an imperfection in a diamond. An argon ion laser was used to produce a beam of radiation having a wavelength of 514.5 nanometers. The beam was used to irradiate a 2 micron diameter spot on the diamond. Resultant scattered Raman radiation was measured using a Jobin-Yvon 3000S spectrometer which measured the intensity of the Raman radiation and recorded it as the spectrograms shown in FIGS. 1 to 4 as graphs of Raman intensity against Raman shift. The diamond had an imperfection which was a pit, 8 microns in a diameter, on its surface. FIG. 1 shows the Raman spectrogram from a region of the diamond distant from the pit. The spectral peak in FIG. 1 is sharp. FIG. 2 shows a spectrogram from the centre of the pit and this shows that the Raman spectral peak is broader due to the imperfection. FIGS. 3 and 4 show spectrograms from the sides of the pit. They show the peak being broader but the broadening is asymmetric. It is envisaged that this peak broadening would, for example, show up as a reduction in the Raman intensity on a photographic record of the diamond produced by the method according to the present invention.

To show that Raman spectroscopy may be used to map the crystal structure of a diamond to show an inclusion the method according to the present invention was used to make a record of a diamond with a simulated inclusion. The diamond had a piece of potassium nitrate on it.

The diamond was held in a holder and irradiated with laser radiation of wavelength 514.5 nanometers from a Spectra Physics 165 argon ion laser. The laser power at the laser head was about 300 mW which reduced to about 25 to 50 mW at the sample. The laser radiation was rotated using spinning mirrors and passed through an annular condenser surrounding a 50 times magnification microscope objective to irradiate an area of the diamond 200 microns in diameter. Resultant scattered Raman radiation was collected by the microscope objective and passed to a Jobin-Yvon Raman spectrometer which was operated in its imaging mode (very wide slits and some lenses retracted) to ensure that the image was transmitted undistorted to a 2-dimensional intensified silicon intensified target (ISIT) camera for detection. By focusing the objective, different planes of the diamond may be mapped. It is envisaged that by using an objective with a large depth of focus the whole diamond may be mapped. The spectrometer passed only radiation characteristic of diamond to the detector. The detector had a 2.5 cm square target with a variable integration time from 1 second to a few minutes. The image on the detector was recorded photographically which showed a bright white image in the regions which were pure diamond and dark regions in the area of the non-diamond inclusion. It is envisaged that a record of the inclusions in the diamond may be produced by recording images from the detector for several orientations of the diamond.

FIG. 5 shows, in schematic form, an apparatus which may be used to map the crystal structure of a diamond and to produce a record of the diamond which may be used for identification purposes.

A diamond (1) is placed in a holder (2) in a beam of monochromatic laser radiation (3). The radiation (3) is provided by a laser (4). It has a wavelength in the range 450 to 650 nanometers and is capable of causing Raman radiation (5) to be scattered from the diamond (1). The scattered Raman radiation (5) is collected by a lens (6), reflected by a beam splitter (7) and to a filter (8) which only passes Raman radiation characteristic of diamond. The intensity of the filtered Raman radiation (9) is measured by a video camera (10) which produces an image on a video monitor (11). The image shows a bright white intensity corresponding to diamond with grey regions indicative of imperfections and black regions indicative of inclusions.

A record of the image on the video monitor is made by photographing it with a camera (12). Several such photographs may be made for different orientations of the diamond to produce a record of the diamond. The record thus produced may be used for future identification purposes.

We claim:

1. A method for mapping the crystal structure of a diamond, the method comprising the steps of (a) placing the diamond in a beam of monochromatic laser radiation capable of causing Raman radiation to be scattered from the diamond, (b) passing the scattered Raman radiation from the diamond through a filter adapted to pass only scattered Raman radiation characteristic of diamond, and (c) measuring the intensity of the filtered Raman radiation at one or more different orientations of the diamond.

2. A method for mapping the crystal structure of a diamond according to claim 1 in which the intensity of the filtered Raman radiation is measured at three mutually perpendicular orientations of the diamond.

3. A method for mapping the crystal structure of a diamond according to claim 1 in which the laser radiation has a wavelength of 450 to 650 nanometers.

4. A method for mapping the crystal structure of a diamond according to claim 1 wherein an imperfection is mapped.

5. A method for mapping the crystal structure of a diamond according to claim 1 wherein an inclusion is mapped.

6. A method for producing a record of a diamond, the method comprising the steps of (a) placing the diamond in a beam of monochromatic laser radiation capable of causing Raman radiation to be scattered from the diamond, (b) passing the scattered Raman radiation from the diamond through a filter adapted to pass only scattered Raman radiation characteristic of diamond, (c) measuring the intensity of the filtered Raman radiation, and (d) recording the intensity of the filtered Raman radiation at one or more different orientations of the diamond.

7. A method for producing a record of a diamond according to claim 6 in which the intensity of the filtered Raman radiation is recorded by electronic, photographic, magnetic or holographic means.

8. A method for producing a record of a diamond according to claim 6 in which the intensity of the filtered Raman radiation is recorded at three mutually perpendicular orientations of the diamond.

9. A record of a diamond whenever produced by a method according to claim 6.

10. A record of a diamond whenever produced by a method according to claim 7.

11. A record of a diamond whenever produced by a method according to claim 8.

12. A record of a diamond according to claim 10 comprising a point by point record of Raman intensities stored in the form of values stored digitally.

13. A record of a diamond according to claim 10 comprising a record of Raman intensitites from the whole of the diamond simultaneously stored photographically.

14. A method for identifying a diamond, the method comprising the steps of (a) placing the diamond to be identified in a beam of monochromatic laser radiation capable of causing Raman radiation to be scattered from the diamond, (b) passing the scattered Raman radiation from the diamond through a filter adapted to pass only scattered Raman radiation characteristic of diamond, (c) measuring the intensity of the filtered Raman radiation, (d) recording the intensity of the filtered Raman radiation at one or more different orientations of the diamond, and (e) comparing the recorded intensities with records of known diamonds whereby the diamond may be identified.

15. A method for identifying a diamond according to claim 14 in which the intensity of the filtered Raman radiation is recorded at three mutually perpendicular orientations of the diamond.

16. An apparatus for producing a record of a diamond, the apparatus comprising in combination (a) means for holding the diamond in a beam of monochromatic laser radiation capable of causing Raman radiation to be scattered from the diamond, (b) means for filtering the resultant scattered Raman radiation, said filter being adapted to pass only scattered Raman radiation characteristic of diamond, (c) means for measuring the intensity of the filtered Raman radiation, and (d) means for recording the intensity of the filtered Raman radiation at one or more different orientations of the diamond to produce a record of the diamond.

17. An apparatus for producing a record of a diamond according to claim 16 wherein said means for holding the diamond is adapted to change the orientation of the diamond.

* * * * *